United States Patent [19]

Burghart et al.

[11] Patent Number: 5,196,184
[45] Date of Patent: Mar. 23, 1993

[54] PHARMACEUTICAL PREPARATION

[76] Inventors: Kurt Burghart, Sägeberg 8, D-2217 Rosdorf, Fed. Rep. of Germany; Walter Burghart, Salmgasse 4, A-1030 Vienna, Austria

[21] Appl. No.: 474,835
[22] PCT Filed: Dec. 28, 1989
[86] PCT No.: PCT/AT89/00130
§ 371 Date: Aug. 27, 1990
§ 102(e) Date: Aug. 27, 1990
[87] PCT Pub. No.: WO90/07345
PCT Pub. Date: Jul. 12, 1990

[30] Foreign Application Priority Data

Dec. 30, 1988 [AU] Australia ............... 3211/88

[51] Int. Cl.⁵ .................................... A61L 9/04
[52] U.S. Cl. ............................. 424/45; 424/70; 424/468; 424/470; 514/317; 514/355; 514/356
[58] Field of Search ............ 424/470, 468, 70, 78, 424/45; 514/356, 317, 355

[56] References Cited

U.S. PATENT DOCUMENTS

| | | | |
|---|---|---|---|
| 4,264,611 | 4/1981 | Berntsson | 514/356 |
| 4,272,516 | 6/1981 | Caldini | 424/70 |
| 4,755,544 | 7/1988 | Makino | 424/468 |
| 4,832,954 | 5/1989 | Sato | 514/355 |
| 4,869,899 | 9/1989 | Burghart | 424/78 |
| 4,871,545 | 10/1989 | Dethlefsen | 424/470 |
| 4,877,799 | 10/1989 | Drejer | 514/317 |

FOREIGN PATENT DOCUMENTS

| | | |
|---|---|---|
| 131228 | 1/1985 | European Pat. Off. |
| 175671 | 5/1985 | European Pat. Off. |
| 0183527 | 11/1985 | European Pat. Off. |
| 240484 | 3/1987 | European Pat. Off. |
| 303490 | 8/1989 | European Pat. Off. |
| 2369867 | 6/1978 | France |

Primary Examiner—Paul R. Michl
Assistant Examiner—William E. Benston
Attorney, Agent, or Firm—Nixon & Vanderhye

[57] ABSTRACT

Pharmaceutical preparation containing Nifedipin as the active substance together with a solution promoter, such as, for example, copolyvidon or polyvinylpyrrolidone and/or glycerol-polyethyleneglycoloxystearate, and with a solvent, such as, for example, alcohols, in particular ethanol, or polyalcohols, as well as, optionally propelling agent for spraying in form of invidually doseable sprays for sublingual adminstriation and additionally containing in the sprayable prepartion 0.5 to 30 percent by weight of benzyl alcohol.

8 Claims, 2 Drawing Sheets

PHARMACEUTICAL PREPARATION

The invention refers to a pharmaceutical preparation containing Nifedipin as the active substance together with a solution promoter, such as, for example, copolyvidon or polyvinylpyrrolidone and/or glycerol-polyethyleneglycoloxystearate, and with a solvent, such as, for example, alcohols, in particular ethanol, or polyalcohols, as well as, optionally, propelling agent for spraying in form of individually doseable sprays for sublingual application.

Medicines containing Nifedipin are known in quite different compositions and for varying types of application. A preparation of the initially mentioned type can, for example, be derived from WO 87/05211. In this preparation according to the known prior art there was introduced an improvement such that Nifedipin being present in a sprayable condition, i.e. being mixed with a propelling agent, remains in solution and will, after the spraying jet, not easily be again precipitated. It is known that Nifedipin is poorly soluble in water and it is further known that a preparation containing Nifedipin as a solution gives rise to precipitating reactions of the Nifedipin with the saliva. In this connection, there was stated in "Deutsche Apothekerzeitung" 128th annual, No. 23, on page 38, that the various known oral dosage forms are occasionally described even in packing enclosures as being sublingually active and that this activity could not be confirmed. Non-sustained released Nifedipin capsules for sublingual application proposed for the acute therapy of the hypertensive crisis and of angina pectoris ought, according to such packing enclosures, result in a more rapid resorption after having broken the capsule with the teeth and having kept the content of the capsule within the mouth for some time, which effect could not be proved in practice. This is attributed to the circumstance that the known preparations are subject to precipitating reactions and that the desired resorption is prevented by a relatively rapid growth of the crystals of the Nifedipin.

For the purpose of accelerating the resorption of pharmaceuticals there has, in particular with respect to dermatological applications, already become known a number of auxiliary substances and there has in particular been proposed benzyl alcohol as a resorption accelerator. A resorption-accelerating activity has, for example, been described in EP-A 183 527 in connection with calcitonin. The preparation having become known from this EP-A 183 527 is a preparation which is resorbed via the mucous membrane of the nose.

From DE-OS 2 209 526, there have become known coronary agents, which are said to be rapidly perlingually resorbable, i.e. via the tongue and via the mucous membrane of the throat. Control tests have now shown that the agents having become known from DE-OS 2 209 526 are, on the one hand, not suitable for the production of a spray even when using propelling agents and result, on the other hand, together with the saliva of the oral cavity in a rapid cristal growth of the Nifedipin and in a precipitation.

The conditions to be considered for the composition of a preparation, which simultaneously shall be suitable to be mixed with a propelling agent, shall mantain the Nifedipin in solution and shall reliably prevent precipitation reactions on dilution with water or the saliva of the mouth, respectively, are partially contradictory, and more recently serious doubts have been expressed with respect to a greater afflux velocity of known preparations containing Nifedipin in case of sublingual application. Such a doubt can, for example, also be taken from "Deutsche Apothekerzeitung" 128th annual, No. 24, page 1268, where can be found the distinct statement that sublingual applications of the known preparations result in lower plasma levels as compared to an oral application. A further problem existing with preparations being intended for being sprayed in doses by means of a pump without using a propelling gas results from the fact that the viscosity and the surface tension of the preparation can, for the purpose of making sure a suitable particle size and distribution of the sprayed material within the mouth, be selected within only narrow limits. Also in this cases, the Nifedipin must be maintained in solution and precipitating reactions need never occur on a dilution with water or with the saliva of the mouth, respectively. In the preparations known up till now, the viscosity required for a spray jet had not been attained and the known preparations, for which a sublingual absorption has been asserted, are ineffective according to the communication of WHO Drug Information Vol. 2, No. 3, 1988. In this connection, the WHO refers to an investigation in Netherlands,, where the sublingual resorption of Nifedipin has been said as being not detectable.

The resorption-accelerating activity of benzyl alcohol could not be confirmed for a number of pharmaceutically active substances, so that benzyl alcohol can equally not in general be said to be a resorption accelerating agent for pharmaceutical active agents.

By means of the pharmaceutical preparation having become known from WO 87/05211 it has become possible to obtain, as compared with the prior art known at this moment, a greater afflux velocity and below the peak curve a surface area increased for approximately 30 percent.

The present invention now aims at providing a pharmaceutical preparation of the initially mentioned type, which is suitable for sublingual application by spraying with or without propelling agent and which results in a still higher afflux velocity and, in particular, in a higher plasma level within short after the application as well as over a longer period. The preparation shall be applicable in individual doses for satisfying therapeutical requirements. Simultaneously, the sublingual resorption shall be increased. For solving this task, the pharmaceutical preparation of the initially mentioned type is, in principle, characterized in that the sprayable preparation contains 0.5 to 30 percent by weight of benzyl alcohol. The local anaesthetic activity of benzyl alcohol is known. For this reason, the amount of benzyl alcohol need not surpass 30 percent by weight at any rate. The use of benzyl alcohol resulted in the surprising recognition that benzyl alcohol can not only be said to be an excellent solvent for Nifedipin and that the addition of benzyl alcohol in case of simultaneous presence of copolyvidon and glycerol-polyethyleneglycoloxy-stearate reliably prevents any precipitation of the Nifedipin when contacting the saliva of the mouth, on the one hand, and, on the other hand, substantially accelerating the perlingual or sublingual resorption, respectively. Within the range indicated according to the invention, an increase of the resorbed amount of Nifedipin for 60 to 70 percent could, as compared with known preparations, be observed-in case of peroral administration and a still considerable increase of the resorption for approximately 30 percent could be observed as compared with the pharmaceutical preparation having become known from WO 87/05211 and not containing benzyl alcohol.

When using propelling agents, benzyl alcohol is in a particularly advantageous manner used in an amount up to 15 percent by weight, preferably up to 10 percent by weight, based on the solution deducting the propelling agent, so that undesired side effects, in particular strong biting in the oral cavity and preponderance of the local anaesthetic effect, are avoided.

It has been found as particularly advantageous that the preparation contains, in a spray jet of 75 to 250 mg, 1 to 7.5 percent by weight Nifedipin, 20 to 40 percent by weight glycerol-polyethyleneglycoloxystearate, 1 to 5 percent by weight benzyl alcohol, 15 to 25 percent by weight ethanol, 0.5 to 5 percent by weight copolyvidon and 30 to 45 percent by weight propelling gas as well as, optionally, pharmaceutically usual sweeting agents and flavourings in an amount of up to 2.5 percent by weight. By means of preparations containing the active substance as well as the resorption acceleration and solvent and, respectively, the solution promotor in the percentages indicated, there is obtained within a short time interval a particularly high afflux velocity and a high plasma level.

A particularly advantageous preparation within the scope of the present invention is essentially characterized in that the preparation contains, in a spray jet of 125 to 200 mg, 5 mg Nifedipin, 40 to 60 mg glycerol-polyethyleneglycoloxystearate, 25 to 40 mg ethanol, 1 to 10 mg copolyvidon, 1 to 15 mg benzyl alcohol and 50 to 70 mg propelling gas as well as, optionally, pharmaceutically usual sweetening agents and flavourings.

When using preparations being sprayable under pump pressure, there have proved as particularly advantageous pharmaceutical preparations which contain in a spraying jet of 50 to 300 mg 1 to 5 percent by weight Nifedipin, 20 to 50 percent by weight glycerol-polyethyleneglycoloxystearate, 2 to 12 percent by weight benzyl alcohol, up to 5 percent by weight copolyvidon, 25 to 60 percent by weight ethanol and/or polethyleneglycol and 0.5 to 35 percent by weight water as well as, optionally, usual sweetening agents and flavourings in amounts up to 2.5 percent by weight. Also with such preparations, there is obtained a particularly rapid afflux and a high plasma level of the active substance within a short time interval after the administration.

Within the scope of the present invention, there has proved as particularly advantageous a preparation being sprayable under pump pressure and containing, in a spray jet of 70 to 150 mg, 1 to 5 mg Nifedipin, 35 to 65 mg glycerol-polyethyleneglycoloxystearate, 1 to 15 mg benzyl alcohol, 2 to 8 mg copolyvidon, 30 to 45 mg ethanol and 1 to 15 mg water as well as, optionally, pharmaceutically usual sweetening agents and flavourings.

Control tests, as are required expressively in particular by the federal health authority (Bundesgesundheitsamt), have shown that relevant statements concerning the mode of action can exclusively be derived from measurements concerning the level of the active agent in blood. Back-flushing tests, which are sporadically found in literature and according to which pharmaceuticals sprayed into the oral cavity are again eluted for the purpose of obtaining a difference value relative to the resorbed portion, prove unavailing in the present case, because in case of precipitation of the active substance the precipitated portion is equally not flushed back during the back-flushing test and is during the subsequent measurement not correctly determined, respectively. The addition of benzyl alcohol in case of a preparation according to the invention did not only result in an improvement of the resorption of the pharmaceutical agent but also in advancing the point of time at which exist pharmaceutically effective blood plasma levels.

The essential advantages of inventive preparations over known preparations result from the comparison tests shown in the drawing and in the examples.

Figure 1:
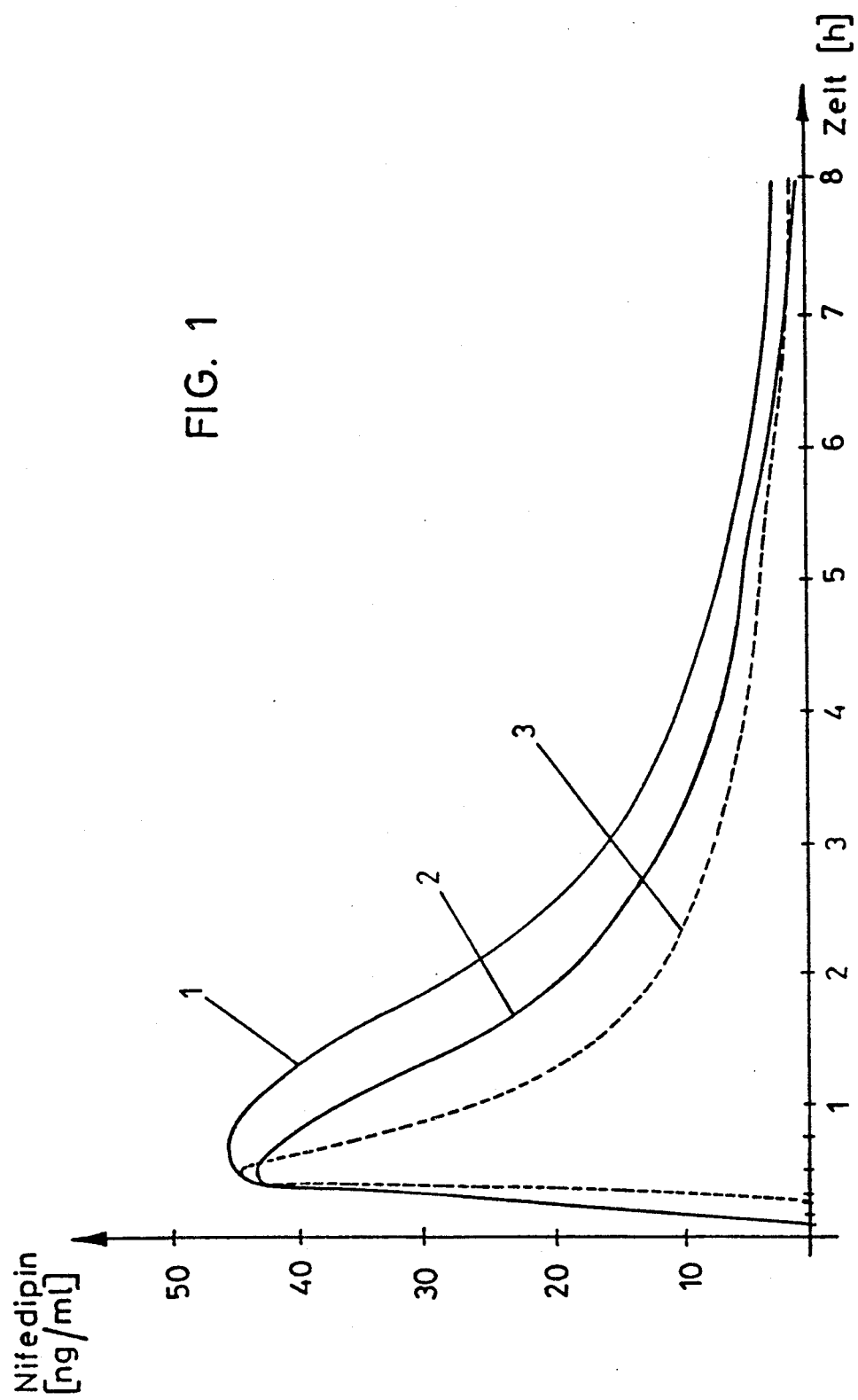
FIG. 1 shows the mean values of the levels of pharmaceuticals derived from three tests performed for determining the relative bioavailability for an inventive preparation containing Nifedipin and for two preparations corresponding to the prior art and containing Nifedipin within 8 hours and FIG. 2 shows the mean values of three tests of the afflux profile of the relative bioavailability for an inventive preparation containing Nifedipin and two preparations according to the prior art and equally containing Nifedipin, within the first half hour after the administration. The measured values are in each case expressed in nanogramms per milliliter on the ordinate and related to the time indicated on the abszissa in hours or minutes respectively.

The control samples used in FIG. 1 were a commercially available capsule to be broken with the teeth and containing 5 mg Nifedipin per capsule, on the one hand, and a sprayable preparation according to the prior art and containing 5 mg Nifedipin, 50 mg glycerol-polyethyleneglycoloxystearate, 30 mg ethanol, 5 mg copolyvidon and 60 mg propellent gas, on the other hand. The inventive preparation used in FIG. 1 contains in total 160 mg propellent gas as spraying agent, 5 mg Nifedipin, 50 mg glycerol-polyethyleneglycoloxystearate, 30 mg ethanol, 5 mg copolyvidon, 10 mg benzyl alcohol and 60 mg of a propellent gas consisting of fluorochlorohydrocarbon as well as, optionally, usual sweetening agents and flavourings.

In FIG. 1, the curve resulting on application of an inventive sprayable preparation is designated by 1. The curve obtained with the sprayable Nifedipin-containing preparation according to the prior art is designated by 2 and the curve obtained with the prior art capsule to be broken by the teeth is designated by 3. The comparison values obtained for the capsule to be broken by the teeth resulted after an oral administration, i.e. after an administration in which the capsule was swallowed without being broken by the teeth. The sprayable preparations 1 and 2 were each sublingually administered. From the comparison test results that for both sprayable reparations, the first levels of Nifedipin in the blood serum could already be detected after 8 minutes. In case of the preparation administered in form of a capsule, a first value of 1,7 ng Nifedipin per milliliter in the serum could only be detected after 15 minutes, at which moment both sprayable preparations resulted in serum values of 20 ng Nifedipin per milliliter in the plasma. After a time interval of 30 minutes till a time interval of 45 minutes after the administration, the plasma levels reach their maximum plasma concentration for both, the preparation having the shape of a capsule, on the one hand, and both sprayable mixtures, on the other hand. The maximum plasma concentrations for the sprayable mixture according to the prior art amounts to 44 ng Nifedipin per milliliter of plasma, while the maximum plasma concentrations for the preparation having the shape of a capsule and for the inventive sprayable mixture is 46 ng Nifedipin per milliliter in the plasma. After 40 minutes, the plasma levels become already strongly reduced in case of the preparation having the shape of a capsule as well as in the case of the sprayable preparation according to the prior art, whereas the inventive sprayable preparation results in its maximum plasma value of 47 ng Nifedipin per milliliter in the plasma only after 50 minutes. After this moment, also the plasma level caused by the inventive preparation becomes reduced, but the gradient of such reduction is, as compared with the preparations according to the prior art, significantly smaller and the plasma concentration remains up to a time interval of 8 hours distinctly greater than those concentrations which result from said both preparations according to the prior art. The mean concentrations of Nifedipin in the plasma are given in the following table.

TABLE 1

| time | Nifedipin in plasma (ng/ml) | | |
|---|---|---|---|
| | capsule | spray of prior art | inventive preparation |
| 10 min | — | 4.1 | 4.5 |
| 15 min | 0.6 | 19.7 | 20.2 |
| 30 min | 45.2 | 43.6 | 45.5 |
| 45 min | 36.6 | 38.7 | 47.0 |
| 60 min | 26.2 | 36.6 | 41.2 |
| 90 min | 15.9 | 25.8 | 37.8 |
| 2 h | 11.8 | 18.4 | 25.7 |
| 3 h | 8.4 | 11.8 | 16.2 |
| 4 h | 4.9 | 7.3 | 10.6 |
| 5 h | 3.8 | 5.0 | 7.2 |
| 6 h | 2.9 | 3.4 | 4.9 |
| 7 h | 1.5 | 2.4 | 3.8 |
| 8 h | 0.6 | 1.4 | 3.0 |

From this Figure as well as from the table shown above, there can, without doubt, be derived that the greatest concentrations of Nifedipin in the plasma can be attained by means of the preparation according to the invention. The area below the curve, which area represents a measure for the amount of active medicine within the body, is in case of the inventive preparation greater for 72 percent as compared with the preparation having the shape of a capsule and greater for 30 percent as compared with the sprayable preparation according to the prior art.

In a series of comparison tests not shown in the drawing, there were tested other substances for which an improvement of the resorption has already been asserted in the literature. Surprisingly there has been shown that the equally known resorption accelerators, i.e. ethyl acetate or benzoic acid, show in combination with Nifedipin no effect or, respectively, improvement of the resorption behavior whatsoever.

Figure 2:
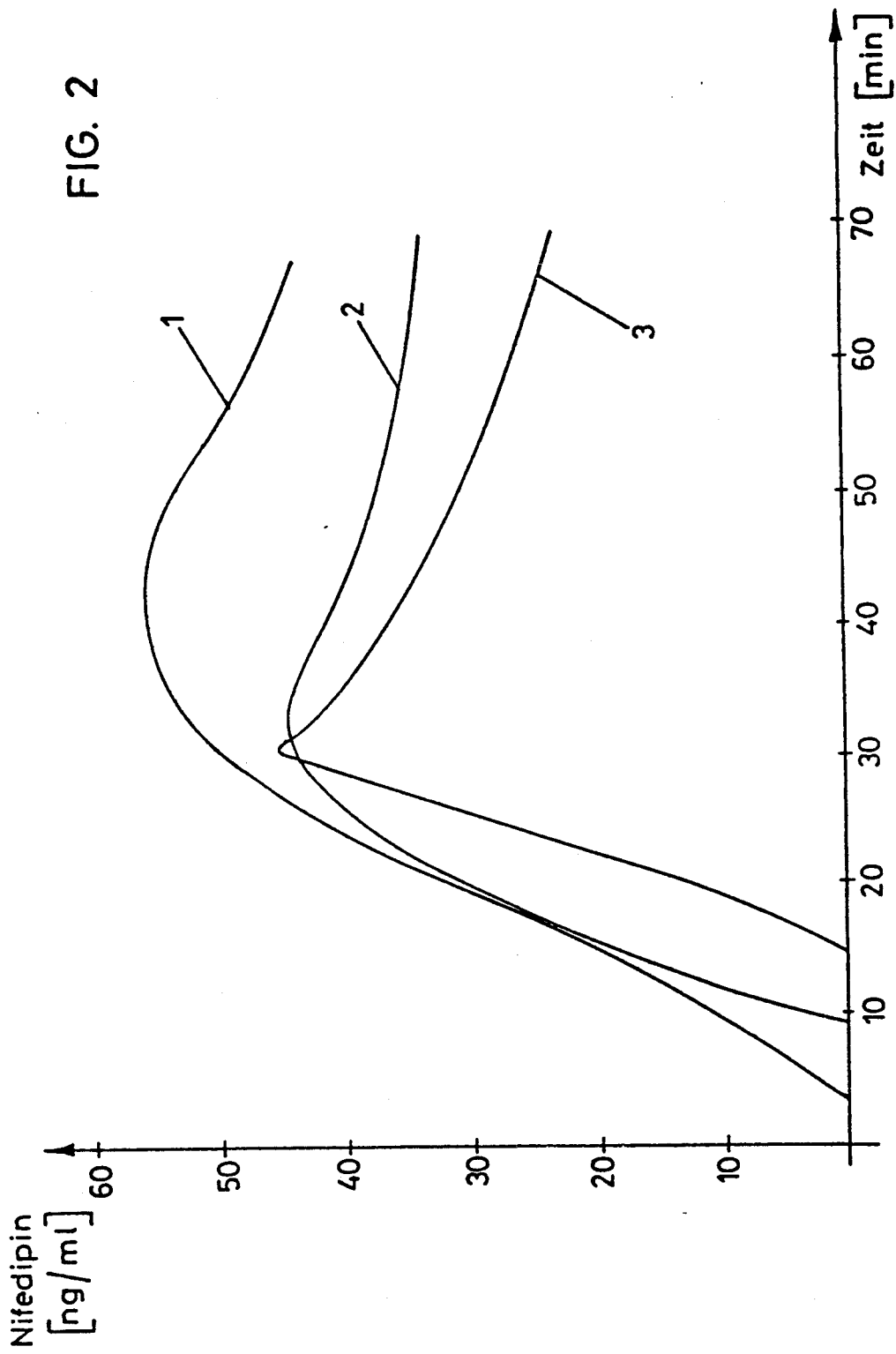

The comparison samples used in FIG. 2 were a commercially available capsule to be broken by the teeth and containing 5 mg Nifedipin per capsule, on the one hand, and a sprayable preparation according to the prior art and containing 5 mg Nifedipin, 50 mg glycerol-polyethyleneglycoloxystearate, 30 mg ethanol, 5 mg copolyvidon and 60 mg propellant gas, on the other hand. The inventive preparation used in FIG. 2 contains in total 160 mg propelling gas as spraying agent, 5 mg Nifedipin, 50 mg glycerol-polyethyleneglycoloxystearate, 30 mg ethanol, 5 mg copolyvidon, 5 mg benzyl alcohol and 65 mg of a propellant gas consisting of fluorochlorohydrocarbons as well as, optionally, usual sweetening agents and flavourings.

In this Figure, the curve reulting on administration of the inventive preparation is designated by 1. The curve resulting from the sprayable preparation according to the prior art is designated by 2, while the curve obtained with the capsule to be broken by the teeth and containing Nifedipin is designated by 3. The comparison values for the capsule to be broken by the teeth resulted on an oral administration of the capsule, during which administration the capsule was swallowed without having been broken by the teeth. The sprayable preparations were each sublingually administered. From the comparison tests results that the sprayable preparation according to the invention resulted already after 4 minutes in a first measureable serum value of 1.13 ng Nifedipin per milliliter plasma. A first serum value for the spray according to the prior art could be measured after 10 minutes and was 4.1 ng Nifedipin per milliliter plasma. At this moment, the plasma level for the inventive sprayable preparation containing benzyl alcohol and Nifedipin was already 11.7 ng Nifedipin per milliliter in the plasma. A first serum value of 0.6 ng Nifedipin per milliliter plasma could be determined only after 15 minutes for the preparation having the shape of a capsule. After 30 minutes the highest plasma level is attained for the capsule as well as for the spray according to the prior art, said plasma level being 45.3 ng Nifedipin per milliliter in the plasma in case of the capsule and 43.7 ng Nifedipin per milliliter in the plasma in case of the spray according to the prior art. At this moment, the serum value measured for the inventive preparation is 51.2 ng Nifedipin per milliliter in the plasma. The inventive sprayable preparation attains its maximum plasma value of 65.0 ng Nifedipin per milliliter in the plasma only after 45 minutes. Subsequently, also the plasma level of the preparation according to the invention becomes reduced, but the gradient of such reduction is not so great as, for example, in case of the prior art preparation having the shape of a capsule. In the following table there is shown the afflux profile of Nifedipin in the plasma.

TABLE 2

| | Afflux profile of Nifedipin in the plasma (ng/ml) | | |
|---|---|---|---|
| time (min) | capsule | spray of prior art | inventive preparation |
| 2 | 0 | 0 | 0 |
| 4 | 0 | 0 | 1.13 |
| 6 | 0 | 0 | 4.7 |
| 8 | 0 | 0 | 8.16 |
| 10 | 0 | 4.1 | 11.7 |
| 15 | 0.6 | 19.6 | 16.5 |
| 20 | 12.8 | 30.9 | 31.1 |
| 30 | 45.3 | 43.7 | 51.2 |
| 45 | 36.0 | 38.8 | 56.0 |
| 60 | 26.2 | 36.5 | 46.9 |

From FIG. 2 as well as from the table shown above, there can clearly be derived that a significantly more rapid afflux of Nifedipin in the plasma can be achieved by means of the sprayable preparation according to the invention. From table 2 as well as from FIG. 2 there can further be clearly derived that not only a more rapid afflux can be achieved with the preparation according to the invention but that also a higher plasma concentration can be obtained within a short time interval as compared with the two preparations according to the prior art. Thus, the maximum plasma concentration ($C_{max}$) of the inventive sprayable preparation is 56.0 ng Nifedipin per milliliter in the plasma and therewith clearly greater than the concentrations of both preparations according to the prior art which result in a maximum plasma concentration of 45.3 ng Nifedipin per milliliter in the plasma in case of the capsule and in a maximum plasma concentration of 43.7 ng Nifedipin per milliliter in the plasma in case of the sprayable preparation.

EXAMPLE 1

Five preparations containing Nifedipin are checked in a test simulating the conditions existing on sublingual administration with respect to their stability under these conditions, i.e. how long no cristallization of Nifedipin can be observed.

|  | Comparison | Pr. 1 | Pr. 2 | Pr. 3 | Pr. 4 |
|---|---|---|---|---|---|
| Nifedipin | 5 mg | 5 mg | 5 mg | 5 mg | 5 mg |
| Glycerol-Polyethylene-glyColoxystearate | 50 mg | 50 mg | 50 mg | 50 mg | 50 mg |
| Ethanol | 30 mg | 35 mg | 30 mg | 30 mg | 30 mg |
| Copolyvidon | 5 mg | 5 mg | 5 mg | 5 mg | 5 mg |
| Benzylalcohol | — | 2 mg | 5 mg | 10 mg | 13 mg |
| Propelling gas | 60 mg | 63 mg | 65 mg | 60 mg | 57 mg |
|  | 150 mg | 160 mg | 160 mg | 160 mg | 160 mg |

0.1 ml water or, respectively, artificial saliva were placed into a watch-glass, whereupon a spray jet of 160 mg or, respectively, 150 mg was applied in case of a preparation according to the prior art and one minute later were added 0.5 ml water or, respectively, artificial saliva. In case of the preparation according to the prior art no cristallisation of Nifedipin cristals could be observed after 15 minutes and in case of all preparations according to the invention the time interval till the formation of the first Nifedipin cristals was in the same time interval in spite of benzyl alcohol having been added. In contrast thereto, immediate cristallization can be observed after an addition of 0.5 ml water or, respectively, artificial saliva if a preparation for capsules according to the prior art, for example the the preparation described in Example 4 of the DE-OS 22 09 526, is subjected to this test.

There were further performed penetration tests with the preparations shown above. In these penetration tests there was determined the penetration of Nifedipin after a time interval of 3 minutes.

For the sprayable preparation according to the prior art, a resorption of 0.13 mg Nifedipin was calculated after the time interval indicated. The inventive preparations containing benzyl alcohol in an increasing amount resulted in a greater resorption of Nifedipin. Thus, a resorption of 0.142 mg was calculated for the preparation 1 containing 2 mg benzyl alcohol per 160 mg spray. A resorption of 0.156 mg was calculated for the preparation 2 containing 5 mg benzyl alcohol. The calculated resorption of 0.185 mg is valid for the preparation 3 containing 10 mg benzyl alcohol per 160 mg of spray. Finally, the resorption was calculated with 0.192 mg for the preparation 4 containing 13 mg benzyl alcohol.

EXAMPLE 2

Two preparations containing Nifedipin but not containing a propelling agent were tested with respect to their spraying behavior as well as with respect to their stability under conditions simulating sublingual application, i.e. how long no cristallization of Nifedipin can be observed.

|  | Pr. 1 | Pr. 2 |
|---|---|---|
| Nifedipin | 5.0 mg | 3.85 mg |
| Glycerol-Polyethylene-glykoloxystearate | 57.6 mg | 44.3 mg |
| Benzyl alcohol | 13.0 mg | 10.0 mg |
| Copolyvidon | 5.0 mg | 3.85 mg |
| Ethanol | 39.0 mg | 34.0 mg |
| Water | 10.4 mg | 4.0 mg |
|  | 130 mg | 100 mg |

0.1 ml water were placed into a watchglass, whereupon a spray jet of 130 mg and 100 mg, respectively, was applied and further 0.5 ml water were added after 2 minutes. Both preparations remained stable for at least 15 minutes under these conditions and no cristallization of Nifedipin could be observed.

Furthermore, both preparations were filled into a container protected against light and being equipped with a Valois-dosing pump, whereupon the dosing accuracy of the valve was checked with the respective spray and the homogeneity of the particles was also checked.

In case of the preparation 1, spraying jets should be obtained having a weight of 130 mg. When discharging 10 spray jets, the average dosage weight obtained was 130.2 mg. The spray jet having the highest sprayed weight weighed 134.7 mg and the spray jet of the lowest weight weighed 124.8 mg. The spray jets showed always a homogeneous particle size.

In case of the preparation 2, a weight of 100 mg per spray jet was intended. When discharging 10 spray jets, a mean dosage weight of 102.1 mg was obtained. The weight of the spray jet having the greatest weight was 105.5 mg, while that of the lowest weight was 96.4 mg.

EXAMPLE 3

Three preparations containing Nifedipin but no propelling agent were checked with respect to their spraying behavior.

|  | Pr. 1 | Pr. 2 | Pr. 3 |
|---|---|---|---|
| Nifedipin | 5.0 | 4.0 | 5.0 |
| Glycerol-Polyethylene-glykoloxystearate | 62.6 | 65.0 | 70.0 |
| Benzyl alcohol | 13.0 | 14.0 | 14.0 |
| Ethanol | 39.0 | 45.0 | 41.0 |
| Water | 10.4 | 17.0 | 10.0 |
|  | 130.0 mg | 140.0 mg | 140.0 mg |

For the purpose of obtaining a spray which can finely and uniformly be sprayed, only glycerol-polyethyleneglycoloxystearate was added to the three compositions as a solution promotor. The preparations were filled into a container protected against light and being equipped with a Valois-dosing pump, whereupon the dosing accuracy of the valve was checked with the respective spray and a homogeneity of the particles was also checked.

In case of the preparation 1 it was intended to obtain spray jets weighing 130 mg. When discharging 10 spray jets, a mean dosage weight of 130.4 mg was obtained. The spray jet having the greatest weight weighed 135.2 mg, while that with the lowest weight weighed 126.5 mg. The spray jets showed at any rate a homogeneous particle size and a uniform fine distribution of the aerosol droplets.

In case of the preparation 2 it was intended to obtain a weight of 140 mg per spray jet. When discharging 10 spray jets, a mean dosage weight of 142.1 mg was obtained. The spray jet having the greatest sprayed weight weighed 143.9 mg, while the weight of the jet having the lowest weight was 138.6 mg.

In case of the preparation 3, it was intended to obtain a weight of 140 mg per spray jet. After discharging 10 spray jets, the mean dosage weight was 140.9 mg per spray jet. The spray jet having the highest sprayed weight weighed 143.1 mg, while the weight of the jet having the lowest weight was 137.2 mg.

All three compositions were characterized by being particularly easily sprayable and by only minor variations of the weight of the spray jet.

EXAMPLE 4

Four preparations containing Nifedipin and intended to be sprayed by pump action were checked with respect to their spraying behavior and also with respect to their stability under conditions simulating a sublingual application.

|  | Pr. 1 | Pr. 2 | Pr. 3 | Pr. 4 |
|---|---|---|---|---|
| Nifedipin | 5.0 | 5.0 | 6.0 | 5.0 |
| Glycerol-Polyethyleneglycoloxystearate | 75.0 | 60.0 | 90.0 | 75.0 |
| Benzyl alcohol | 15.0 | 15.0 | 10.0 | 15.0 |
| Ethanol | 70.0 | 50.0 | 160.0 | 104.0 |
| Polyethylene- | — | 40.0 | — | 70.0 |
| Water | 34.0 | 79.0 | 30.0 | 30.0 |
| Copolyvidon | 1.0 | 1.0 | 4.0 | 1.0 |
|  | 200.0 mg | 250.0 mg | 300.0 mg | 300.0 mg |

0.1 ml water were placed into a watchglass, whereupon a spray jet of 250 mg or, respectively, 300 mg was discharged and 0.5 ml water were added 2 minutes later. All preparations remained stable under these conditions for a time interval of at least 15 minutes and no cristallization of the Nifedipin could be observed.

The preparations were filled into a container protected against light and equipped with a Valois-dosing pump, whereupon the dosing accuracy of the valve was checked with the respective spray and also the homogeneity of the particles was checked.

In case of the preparation 1 it was intended to obtain spray jets having a weight of 200 mg. When discharging 10 jets, a mean dosing weight of 200.9 mg was obtained. The spray jet having the highest sprayed weight weighed 203.1 mg, while that with the lowest weight weighed 196.1 mg. The spray jets showed a homogeneous particle size in any case.

In the case of the preparation 2 it was intended to obtain a spray jet having a weight of 250 mg. When discharging 10 spray jets, a mean dosage weight of 251.7 mg was obtained. The spray jet having the highest sprayed weight weighed 254.3 mg, while the weight of the spray jet having the lowest weight was 247.0 mg.

With the preparation 3 it was intended to obtain spray jets weighing 300 mg. When discharging 10 spray jets, there was obtained a mean sprayed weight of 301.3 mg, the spray jet having the lowest weight weighing 298.4 mg and that having the highest sprayed weight weighed 303.6 mg.

In the case of the preparation 4 it was intended to obtain spray jets weighing 300 mg. When discharging 10 spray jets, a mean dosage weight of 300.8 mg was obtained. The spray jet having the highest sprayed weight weighed 302.1 mg, while that having the lowest weight weighed 297.9 mg.

What is claimed is:

1. A sprayable pharmaceutical preparation, comprising, in a spray jet, 1 to 7.5% by weight Nifedipin, 20 to 40% by weight glycerol-polyethyleneglycol oxystearate, 1 to 5% by weight benzyl alcohol, 15 to 25% by weight ethanol, 0.5 to 5% by weight copolyvidon and 30 to 45% by weight of a propelling agent.

2. A sprayable pharmaceutical preparation according to claim 1, and further comprising pharmaceutically acceptable agents and flavorings in an amount up to 2.5% by weight.

3. A sprayable pharmaceutical preparation according to claim 1, wherein the preparation contains, in a spray jet, 2.5 to 4% by weight Nifedipin, 30 to 32% by weight glycerol-polyethyleneglycoloxystearate, 16 to 20% by weight ethanol, 0.8 to 5% by weight copolyvidon, 0.8 to 7.5% by weight benzyl alcohol and 35 to 40% by weight of a propelling agent.

4. A sprayable pharmaceutical preparation according to claim 3, wherein said preparation further comprises pharmaceutically acceptable sweetening agents and flavorings.

5. A sprayable pharmaceutical preparation sprayable under pump pressure, comprising, in a spray jet, 1 to 5% by weight Nifedipin, 20 to 50% by weight glycerol-polyethyleneglycol oxystearate, 2 to 12% by weight benzyl alcohol, up to 5% by weight copolyvidon, 25 to 60% by weight ethanol or polyethyleneglycol and 0.5 to 35% by weight water.

6. A sprayable pharmaceutical preparation according to claim 5, wherein said preparation further comprises sweetening agents and flavorings in an amount up to 2.5% by weight.

7. A sprayable pharmaceutical preparation sprayable under pump pressure, comprising, in a spray jet, 1.4 to 3.3% by weight Nifedipin, 43 to 50% by weight glycerol-polyethyleneglycol oxystearate, 1.4 to 10% by weight benzyl alcohol, 2.8 to 5.3% by weight copolyvidon, 30 to 43% by weight ethanol and 1.4 to 10% by weight water.

8. A sprayable pharmaceutical preparation according to claim 7, wherein the preparation also comprises pharmaceutically acceptable sweetening agents and flavorings.

* * * * *

UNITED STATES PATENT AND TRADEMARK OFFICE
CERTIFICATE OF CORRECTION

PATENT NO. : 5,196,184
DATED : March 23, 1993
INVENTOR(S) : BURGHART et al It is certified that error appears in the above-identified patent and that said Letters Patent is hereby corrected as shown below:

On title page, item [30] delete

"Dec. 30, 1988 [AU] Australia.....3211/88" and replace by

--Dec. 30, 1988 [AT] Austria.....3211/88--

Signed and Sealed this

Eighth Day of February, 1994

Attest:

BRUCE LEHMAN

*Attesting Officer*  *Commissioner of Patents and Trademarks*